United States Patent [19]

Rossignol et al.

[11] 3,957,812
[45] May 18, 1976

[54] DERIVATIVES OF 2-PHENOXYACETAMIDO-5-NITRO-THIAZOLE

[75] Inventors: Jean-Francois Rossignol, Paris; Raymond Cavier, Villejuif, both of France

[73] Assignee: S.P.R.L. Phavic, Mouscron, Belgium

[22] Filed: Aug. 29, 1974

[21] Appl. No.: 501,579

[30] Foreign Application Priority Data

Aug. 29, 1973 United Kingdom............... 40626/73

[52] U.S. Cl............................ 260/306.8 R; 424/270
[51] Int. Cl.²........................................ C07D 277/58
[58] Field of Search.............................. 260/306.8 R

[56] References Cited
UNITED STATES PATENTS

| | | | |
|---|---|---|---|
| 3,113,947 | 12/1963 | Currie.......................... | 260/306.8 R |
| 3,246,975 | 4/1966 | Hopkins et al............... | 260/306.8 R |
| 3,734,923 | 5/1973 | Dowding et al.............. | 260/306.8 R |
| 3,801,588 | 4/1974 | Harrington et al........... | 260/306.8 R |
| 3,862,163 | 1/1975 | Boroschewski et al. ..... | 260/306.8 R |

Primary Examiner—Alton D. Rollins
Assistant Examiner—Mary Vaughn
Attorney, Agent, or Firm—Sughrue, Rothwell, Mion & Zinn

[57] ABSTRACT

The new 2-phenoxyacetamido-5-nitro-thiazole represented by the formula:

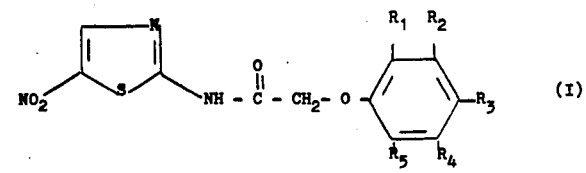

in which one of the symbols $R_1$, $R_2$, $R_3$, $R_4$ and $R_5$ represents a halogen, preferably chlorine, bromine or fluorine, or a lower alkyl radical containing preferably 1 to 3 carbon atoms, or a trifluoromethyl radical, the remaining symbols representing hydrogen are interesting parasiticides, bacteriostatic agents and fungistatic agents.

3 Claims, No Drawings

DERIVATIVES OF 2-PHENOXYACETAMIDO-5-NITRO-THIAZOLE

SUMMARY OF THE INVENTION

This invention relates to new 2-phenoxyacetamido-5-nitro-thiazoles, as well as the preparation and use of said compounds in the pharmaceutical dield.

The new compounds according to this invention may be represented by the following general formula:

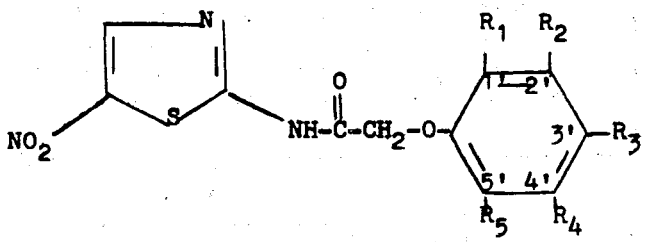

(I)

in which at least one of the symbols $R_1$, $R_2$, $R_3$, $R_4$ and $R_5$ represents a halogen or a lower alkyl or trifluoromethyl radical, the remaining symbols representing hydrogen.

This invention relates also to a process for preparing the new compounds of formula (I), as well as to compositions containing at least one of said compounds, as active parasiticidal, bacteriostatic and/or fungistatic ingredient.

DETAILED DESCRIPTION OF THE INVENTION

Among the new compounds according to this invention, the following may be cited by way of examples:

2-(3'-chlorophenoxyacetamido)-5-nitrothiazole;
2-(1',3'-dichlorophenoxyacetamido)-5-nitro-thiazole;
2-(3'-bromophenoxyacetamido)-5-nitrothiazole;
2-(1'-isopropyl-3'-chloro-4'-methyl-phenoxyacetamido)-5-nitrothiazole;
2-(3'-fluoro-phenoxyacetamido)-5-nitrothiazole;
2-(2'-trifluoromethyl-4'-trifluoromethyl-phenoxyacetamido)-5-nitrothiazole;
2-(1',2',3',4',5'-pentafluoro-phenoxyacetamido)-5-nitrothiazole;
2-(1'-chloro-3',4'-dimethylphenoxyacetamido)-5-nitrothiazole;
2-(2'-trifluoromethyl-3'-methylphenoxyacetamido)-5-nitrothiazole;
2-(2'methyl-3'-chlorophenoxyacetamido)-5-nitrothiazole;
2-(2',4'-dichloro-phenoxyacetamido)-5-nitrothiazole.

The new compounds of formula (I) are prepared, according to this invention, by reacting 2-amino-5-nitrothiazole of the formula:

(II)

with a phenoacetyl halide of the formula:

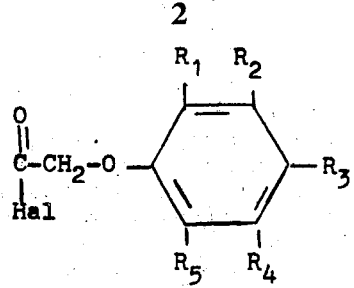

in which Hal represents a halogen atom, preferably a chlorine atom, whereas $R_1$, $R_2$, $R_3$, $R_4$ and $R_5$ have the above meanings, in the presence of triethylamine.

The reaction between the 2-amino-5-nitrothiazole of formula (II) and the phenoxyacetyl halide of formula (III) is preferably carried out at room temperature by adding slowly triethylamine to a stirred solution of the compounds of formulae (II) and (III) in a solvent, such as anhydrous tetrahydrofuran, by stirring the reaction mixture and by pouring it in distilled water, the stirring being continued until the desired product crystallizes.

It has been found that the compounds of formula (I) may be used as parasiticides, namely for the control of *Trichomonas vaginalis*, *Entomoeba dysenteriae*, *Syphacia obvelata* and *Hymenolepis nana*.

It has also been found that the compounds of formula (I) may be used as bacteriostatic and fungistatic agents, namely for the control of the following bacteria and fungi:

|  |  |  | Abbreviation |
|---|---|---|---|
| Bacteria | | | |
| *Staphylococcus* |  | 209 P | Sta. or S. | 209 P |
| *Staphylococcus* | ATCC | 12715 | Sta. or S. | ATCC 12715 |
| *Staphylococcus* |  | 8006 | Sta. or S. | 8006 |
| *Staphylococcus* |  | 101 | Sta. or S. | 101 |
| *Escherichia coli* | IPA | 223 | E. Coli | IPA 223 |
| *Escherichia coli* | OIII B | 4 | E. Coli | OIII B 4 |
| *Streptococcus faecalis* | ATCC | 9790 | S.faec. | ATCC 9790 |
| *Shigella dysenteriae* |  | 3410 | S. | 3410 |
| *Shigella sonnei* |  | 8025 | S. | 8025 |
| *Pseudomonas aeruginosa* |  | 8194 | Pseudo. | 8194 |
| *Proteus vulgaris* |  | 8181 | P. vulg. | 8181 |
| *Proteus morganii* | IP | 53185 | P. morg. | IP 53185 |
| *Enterococcus* |  | 504 | E. | 504 |
| *Enterococcus* |  | 8043 | E. | 8043 |
| *Enterococcus* |  | 9790 | E. | 9790 |
| Fungi | | | |
| *Trichophyton mentagrophytes* |  |  | T.m. |  |
| *Trichophyton rubrum* |  |  | T.r. |  |
| *Microsporum felineum* |  |  | M.f. |  |
| *Microsporum audouini* |  |  | M.a. |  |
| *Epidermo flocosum* |  |  | E.f. |  |

This invention relates therefore also to compositions to be used for the control of parasites, bacteria or fungi, said compositions containing at least one compound of formula (I), together with a suitable pharmaceutical carrier.

EXAMPLES 1 to 12

The compounds listed in Table I have been prepared by the following method:

To a solution of one mole of a phenoxyacetyl chloride formula (III) and one mole of carefully purified 2-amino-5-nitrothiazole in 200 ml of anhydrous tetrahydrofuran at room temperature, one mole of triethylamine has been slowly added (about 10 minutes), while stirring. The reaction mixture which became slightly warn has been stirred during 45 minutes and then poured, under agitation, into 2 liters of distilled water. The stirring has been continued until the precipitation of the desired compound stopped. The obtained precipitate was dried, washed with water, again dried and recrystallized from ethanol.

MEDIUM

A liquide Sabouraud medium having the following composition is used:

| | |
|---|---|
| peptone (Oxoid) | 10 grams |
| anhydrous glucose | 20 grams |
| distilled water q.s. for | 1,000 ml. |

If necessary, the pH is adjusted at 6.4 and the medium is sterilized.

Solubilization of the compounds to be tested

The compounds are dissolved in dimethylformamide to which polyethylene glycol is sometimes added. From the mother-liquor, successive diluted solutions are pre-

TABLE I

| Ex Nr | Code Number | Substituents in formula I | Melting point °C | Formula | | Mol Weight | ANALYSIS Calculated | | | | |
|---|---|---|---|---|---|---|---|---|---|---|---|
| | | | | | | | C | H | N | S | Hal |
| 1 | PH 5927 | $R_1=R_2=R_4=R_5=H$; $R_3=Cl$ | 231 | $C_{11}H_8N_3O_4SCl_2$ | = | 313,5 | 42.10 | 2.55 | 13.39 | 10.20 | 11.32 |
| 2 | PH 6091 | $R_1=R_3=Cl$; $R_2=R_4=R_5=H$ | 196 | $C_{11}H_7N_3O_4SCl_2$ | = | 348 | 37.93 | 2.01 | 12.06 | 9.19 | 20.40 |
| 3 | PH 6092 | $R_1=R_2=R_4=R_5=H$; $R_3=Br$ | 235 | $C_{11}H_8N_3O_4SBr$ | = | 358 | 36.87 | 2.23 | 11.73 | 8.93 | 22.34 |
| 4 | PH 6099 | $R_1=C_3H_7$; $R_2=R_5=H$: $R_3=Cl$; $R_4=CH_3$ | 178 | $C_{15}H_{16}N_3O_4SCl$ | = | 369,5 | 48.71 | 4.33 | 11.36 | 8.66 | 9.60 |
| 5 | PH 6159 | $R_1=R_4=Cl$; $R_2=R_3=R_5=H$ | 246 | $C_{11}H_7N_3O_4SCl_2$ | = | 348 | 37.93 | 2.02 | 12.06 | 9.19 | 20.40 |
| 6 | PH 6160 | $R_1=R_2=R_4=R_5=H$; $R_3=F$ | 188 | $C_{11}H_8N_3O_4SF$ | = | 297 | 44.44 | 2.69 | 14.14 | 10.77 | 6.39 |
| 7 | PH 6167 | $R_1=R_3=R_5=H$; $R_2=R_4=CF_3$ | 207 | $C_{13}H_7N_3O_4SF_6$ | = | 415 | 37.59 | 1.68 | 10.12 | 7.71 | 27.46 |
| 8 | PH 6168 | $R_1=R_2=R_3=R_4=R_5=F$ | 154 | $C_{11}H_4N_3O_4SF_5$ | = | 369 | 35.77 | 1.08 | 11.38 | 8.67 | 25.74 |
| 9 | PH 6182 | $R_1=R_3=R_5=H$; $R_2=R_4=Cl$ | 175 | $C_{11}H_8N_3O_4SCl_2$ | = | 349 | 37.82 | 2.29 | 12.03 | 9.16 | 20.34 |
| 10 | PH 6305 | $R_1=Cl$;$R_2=R_5=H$;$R_3=R_4=CH_3$ | 185 | $C_{13}H_{11}N_3O_4SCl_2$ | = | 340,5 | 45.81 | 3.23 | 12.33 | 9.39 | 10.42 |
| 11 | PH 6306 | $R_1=R_4=R_5=H$;$R_2=CF_3$;$R_3=CH_3$ | 141 | $C_{12}H_8N_4O_6SF_3$ | = | 391 | 36.92 | 1.53 | 14.32 | 8.18 | 14.57 |
| 12 | PH 6314 | $R_1=R_4=R_5=H$; $R_2=CH_3$;$R_3=Cl$ | 177 | $C_{12}H_9N_3O_4SCl$ | = | 326.5 | 44.10 | 2.75 | 12.86 | 9.80 | 10.87 |

| Ex Nr | Code Number | Substituents in formula I | Melting point °C | Formula | | Mol Weight | ANALYSIS Found | | | | |
|---|---|---|---|---|---|---|---|---|---|---|---|
| | | | | | | | C | H | N | S | Hal |
| 1 | PH 5927 | $R_1=R_2=R_4=R_5=H$; $R_3=Cl$ | 231 | $C_{11}H_8N_3O_4SCl_2$ | = | 313,5 | 42.02 | 2.42 | 13.40 | 10.18 | 11.27 |
| 2 | PH 6091 | $R_1=R_3=Cl$; $R_2=R_4=R_5=H$ | 196 | $C_{11}H_7N_3O_4SCl_2$ | = | 348 | 37.84 | 1.92 | 11.95 | 9.12 | 20.32 |
| 3 | PH 6092 | $R_1=R_2=R_4=R_5=H$; $R_3=Br$ | 235 | $C_{11}H_8N_3O_4SBr$ | = | 358 | 36.81 | 2.17 | 11.69 | 8.82 | 22.29 |
| 4 | PH 6099 | $R_1=C_3H_7$; $R_2=R_5=H$: $R_3=Cl$; $R_4=CH_3$ | 178 | $C_{15}H_{16}N_3O_4SCl$ | = | 369.5 | 48.69 | 4.28 | 11.29 | 8.52 | 9.54 |
| 5 | PH 6159 | $R_1=R_4=Cl$; $R_2=R_3=R_5=H$ | 246 | $C_{11}H_7N_3O_4SCl_2$ | = | 348 | 37.87 | 1.97 | 12.04 | 9.01 | 20.27 |
| 6 | PH 6160 | $R_1=R_2=R_4=R_5=H$; $R_3=F$ | 188 | $C_{11}H_8N_3O_4SF$ | = | 297 | 44.38 | 2.59 | 14.09 | 10.69 | 6.27 |
| 7 | PH 6167 | $R_1=R_3=R_5=H$; $R_2=R_4=CF_3$ | 207 | $C_{13}H_7N_3O_4SF_6$ | = | 415 | 37.48 | 1.62 | 10.06 | 7.62 | 27.41 |
| 8 | PH 6168 | $R_1=R_2=R_3=R_4=R_5=F$ | 154 | $C_{11}H_4N_3O_4SF_5$ | = | 369 | 35.69 | 1.02 | 11.22 | 8.60 | 25.69 |
| 9 | PH 6182 | $R_1=R_3=R_5=H$; $R_2=R_4=Cl$ | 175 | $C_{11}H_8N_3O_4SCl_2$ | = | 349 | 37.76 | 2.19 | 12.05 | 9.10 | 20.28 |
| 10 | PH 6305 | $R_1=Cl$;$R_2=R_5=H$;$R_3=R_4=CH_3$ | 185 | $C_{13}H_{11}N_3O_4SCl_2$ | = | 340,5 | 45.72 | 3.14 | 12.29 | 9.31 | 10.46 |
| 11 | PH 6306 | $R_1=R_4=R_5=H$;$R_2=CF_3$;$R_3=CH_3$ | 141 | $C_{12}H_8N_4O_6SF_3$ | = | 391 | 36.83 | 1.47 | 14.26 | 8.11 | 14.49 |
| 12 | PH 6314 | $R_1=R_4=R_3=H$; $R_2=CH_3$;$R_3=Cl$ | 177 | $C_{12}H_9N_3O_4SCl$ | = | 326,5 | 44.07 | 2.69 | 12.78 | 9.72 | 10.89 |

BIOLOGICAL TESTS

Biological tests have been performed with a great number of compounds of formula (I) using the following techniques: (1) Test for amoebicidal activity described by R. CAVIER, Ann. pharm. franc., 1960, 18, pages 583–589 and by R. CAVIER, and J. CENAC, Bull. Soc. Path. exot. 1972, 65, pages 399–404. (2) Test for trichomonacidal activity described by R. CAVIER and P. BUOT, Ann. pharm. franc., 1964, 22, pages 211–216 and by R. CAVIER and J. CENAC, Semaine des Hopitaux, 1972, 48, pages 391–394). (3) Tests for anthelminthics described for nematodes (such as *Syphacia obvelata*) by R. CAVIER, Bull. Soc. Path. exot., 1962, 55, pages 412–417 and, for cestodes (such as *Hymenolepis nana*), by R. CAVIER, Ann. pharm. franc., 1956, 14, pages 545–552 and by R. CAVIER and M. J. NOTTEGHEM, Ann. pharm. franc. 1968, 28, pages 603–606.

(4) Method for determining fungistatic doses:

pared in the liquid Sabouraud medium, so as to obtain concentrations of 1, 3, 10, 30 100 and 300 mg per ml. For the first dilution, one should not add more than 10% of the mother-liquor to the Sabouraud medium. Subsequently 9 ml per tube of the various solutions in the liquid Sabouraud medium are distributed.

Reference tubes corresponding to the highest solvent concentrations are also prepared.

SEEDING

For dermatophytes:

Cultures of the various dermatophyte strains on Sabouraud gelose medium are prepared. From 1 to 2 months old cultures, homogeneous suspensions of said cultures in the liquid Sabouraud medium are prepared, the obtained suspensions being stirred in the presence of glass pearls having a light transmission of about 40%.

One drop of said suspension is introduced in the tubes containing the various concentrations of the compound to be tested.

For yeasts:

The same method as for dermatophytes is used except that 2 to 3 weeks old cultures on Sabouraud gelose medium are used.

INCUBATION at 25°C ± 2°C in the dark

READING

Direct reading after
5 days of incubation for yeasts
10 days of incubation for dermatophytes.

(5) Method for determining bacteriostatic doses

MEDIUM

A common gelose medium of the following composition is used.

| | |
|---|---|
| Bacteriological peptone (Oxoid) | 10 grams |
| meat extract (Liebig) | 5 grams |
| sodium chloride | 5 grams |
| distilled water q.s. for | 1,000 ml |

The pH is adjusted at 7.2 and the medium is sterilized during 30 minutes at 120°C.

Solubilization of the compounds to be tested

The same method as for the determination of fungistatic doses is used, except that the various dilutions of each compound are added to the gelose medium, the solvent concentration never exceeding 3%. Tubes containing 1, 3, 10, 30, 100, and 300 mg of the compounds per ml are prepared.

SEEDING

Cultures of each strain in the liquid medium are prepared and, after 24 hours of incubation at 37°C, dilutions of these cultures in ordinary broth are prepared as follows:

| | |
|---|---|
| Staphylococcus aureus 209 P | 1 drop in 20 ml |
| Enterococcus 9790 | 1 drop in 20 ml |
| Escherichia coli OIII B 4 | 1 drop in 20 ml |
| Shigella dysenteriae 3410 | 1 drop in 10 ml |
| Proteus morganii IP 53185 | 1 drop in 10 ml |
| Pseudomonas aeruginosa 8194 | 1 drop in 20 ml |

By means of these dilutions, scratches of a length of 4 to 5 cm are made on the previously dried surface of the gelose medium to which various amounts of the compound to be tested have been added.

INCUBATION at 37°C during 24 hours

DIRECT READING after 24 hours.

Following Tables II and III give the results of the tests which have been made with various compounds of the formula (I) on a number of parasites, bacteria and fungi.

TABLE II

| | BIOLOGICAL PROPERTIES | | | | | | | | | | | |
|---|---|---|---|---|---|---|---|---|---|---|---|---|
| | PARASITOLOGY | | | | | | | | | | | |
| Compound | Trichomonas vaginalis | | Entomoeba dysenteriae | | Syphacia obvelata | | | | Hymenolepis nana. | | | |
| Code number | starting activity | lethal action | starting activity (5) | lethal action | N° (1) | + (2) | D (3) | % (4) | N° (1) | + (2) | D (3) | % (4) |
| PH 5927 | 1 to 1.25 | 12.5 | 1 to 1.25 | 25 to 50 | 10 | 0 | 3 | 30 | 10 | 0 | 0 | 0 |
| PH 6091 | 1 to 2 | | 50 to 100 | | 10 | 0 | 2 | 20 | 10 | 0 | 3 | 30 |
| PH 6092 | 100 | | 100 | | 10 | 0 | 1 | 10 | 10 | 0 | 1 | 10 |
| PH 6099 | 100 | | 10 | | 10 | 0 | 2 | 20 | 10 | 0 | 4 | 40 |
| PH 6159 | 50 to 100 | | 5 to 10 | | 10 | 0 | 0 | 0 | 10 | 0 | 2 | 20 |
| PH 6160 | 50 to 100 | | 5 to 10 | | 10 | 0 | 0 | 0 | 10 | 0 | 0 | 0 |
| PH 6167 | 50 to 100 | | 100 | | 10 | 0 | 4 | 40 | 10 | 0 | 7 | 70 |
| PH 6168 | 50 to 100 | | 100 | | 10 | 0 | 0 | 0 | 10 | 0 | 2 | 20 |
| PH 6182 | 50 to 100 | | 2.5 | | | | | | 10 | 0 | 0 | 0 |
| PH 6305 | 5 to 10 | | 10 | | 10 | 0 | 1 | 10 | 10 | 0 | 0 | 0 |
| PH 6306 | 5 to 10 | | 5 | | 10 | 0 | 0 | 0 | 10 | 0 | 0 | 0 |
| PH 6314 | 2.5 | | 10 | | 10 | 0 | 0 | 0 | 10 | 0 | 0 | 0 |

(1) Number of subjects
(2) Number of dead subjects
(3) Number of subjects from which the parasite has been eradicated
(4) Percentage of activity
(5) in mμ/ml

TABLE III

| | BIOLOGICAL PROPERTIES | | | | | | | | | | |
|---|---|---|---|---|---|---|---|---|---|---|---|
| | Doses in μg/ml. | | | | | | | | | | |
| Compound | fungi | | | | | bacteria | | | | | |
| Code number | T.m | M.f. | M.a. | E.f. | T.r. | S. 209 P | E. 9790 | O.III B 4 | S. 3410 | P. morg. | Pseudo 8194 |
| PH 5927 | 30 | 00 | | 10 | | 100 | 0 | | 0 | 0 | 0 |
| PH 6091 | 3 | 30 | | 1 | | 3 | 0 | 0 | 0 | 0 | 0 |
| PH 6092 | 100 | 0 | | 0 | | 10 | 0 | 0 | 0 | | |
| PH 6099 | 0.5 to 1 | | 0.1 | 0.5 to 1 | 2 | 3 | 300 | 0 | 300 | 0 | 0 |
| PH 6159 | 30 | — | | 0 | | 0 | 0 | 0 | 0 | 0 | 0 |
| PH 6160 | 4 | | 4 | 1 | 4 | 10 | 0 | 0 | 100 | 0 | 0 |
| PH 6167 | 1 | 0 | | 1 | | 3 | 10 | 0 | 0 | | 0 |
| PH 6168 | 1 | — | 3 | 1 | | 10 | 10 | 300 | 300 | 300 (8181) | 0 |
| PH 6182 | 1 | — | 3 | 1 | | 10 | 0 | 0 | 0 | 0 | 0 |
| PH 6305 | 0 | 0 | | 0 | | 0 | 0 | 0 | 0 | 0 | 0 |
| PH 6306 | 1 | 10 | | 30 | | 10 | 100 | 0 | 0 | 0 | 0 |
| PH 6314 | 0 | 0 | | 0 | | 3 | 0 | 0 | 0 | 0 | 0 |

The above tests clearly show that the compound of formula (I) may be useful for the treatment of various parasitic diseases, such as trichomoniasis, amoebiasis and oxyurasis, as well as bacteriostatic and fungistatic agents.

For the treatment of parasitic diseases, the compound of formula (I) may be used together with usual pharmaceutical carriers in tablets, capsules, syrups and gynaecological ovules.

For the treatment of mycoses and bacterial infections, the compounds of formula (I) may be used together with usual pharmaceutical carriers in tablets, capsules, ointment and suppositories.

When used as anthelminthics, tablets containing about 500 mg of a compound of formula (I) may be administered to adults at a dose of 2 to 4 tablets per day.

It is pointed out that the presence of the $R_1$, $R_2$, $R_3$, $R_4$ or $R_5$ substituents (other than hydrogen) in the compounds of formula (I) is critical for the parasitological bacteriostatic and fungistatic activities of the compounds, since tests have shown that 2-phenoxyacetamido-5-nitro-thiazole, which is a known compound of formula (I) wherein $R_1$, $R_2$, $R_3$, $R_4$ and $R_5$ represent hydrogen, has no activity against *Trichomonas vaginalis* and *Entomoeba dysenteriae*, nor against bacteria and fungi.

Toxicity investigations have shown that the compounds of formula (I) have a very low acute toxicity.

The acute toxicity of compound PH 5927 is more than 4500 mg/kg ($LD_{50}$) after intraperitoneal administration to mice, whereas the acute toxicity of compound PH 6099 is of about 200 mg/kg ($LD_{50}$) after intraperitoneal administration to mice.

The $LD_{50}$ of compounds PH 6099 and 5927, when orally administered to mice, is of more than 4000 mg/kg.

What we claim is:

1. New 2-phenoxyacetamido-5-nitro-thiazoles of the general formula:

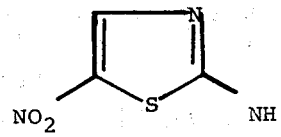 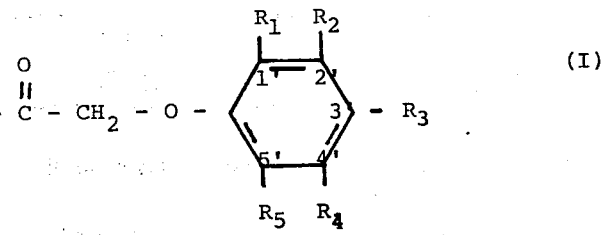

in which at least one of the symbols $R_1$, $R_2$, $R_3$, $R_4$ and $R_5$ represents chlorine, bromine or fluorine or a lower alkyl containing 1 to 3 carbon atoms or trifluoromethyl radical, the remaining symbols representing hydrogen.

2. 2-(3'-chlorophenoxyacetamido)-5-nitrothiazole.
3. 2-(1'-isopropyl-3'-chloro-4'-methyl-phenoxyacetamido)-5-nitrothiazole.

* * * * *